(12) United States Patent
Donahue

(10) Patent No.: US 6,444,963 B1
(45) Date of Patent: Sep. 3, 2002

(54) MICROWAVE DEODORIZER

(76) Inventor: Raymond G. Donahue, 1735 Foothill Dr., Glendale, CA (US) 91201

( * ) Notice: Subject to any disclaimer, the term of this patent is extended or adjusted under 35 U.S.C. 154(b) by 0 days.

(21) Appl. No.: 09/785,686

(22) Filed: Feb. 16, 2001

(51) Int. Cl.$^7$ .......................... H05B 6/80; B65D 81/34; F24C 7/02
(52) U.S. Cl. ...................... 219/678; 219/756; 219/725; 239/56; 422/120; 422/121; 261/DIG. 65
(58) Field of Search ................................. 219/678, 679, 219/756, 757, 725, 734, 735; 239/55, 56; 422/120, 121, 305, 307; 261/DIG. 65

(56) References Cited

U.S. PATENT DOCUMENTS

| | | | |
|---|---|---|---|
| 4,493,011 A | 1/1985 | Spector | |
| 4,544,592 A | 10/1985 | Spector | |
| 4,647,433 A | 3/1987 | Spector | |
| 4,735,358 A | 4/1988 | Morita et al. | |
| 4,965,490 A | 10/1990 | Ratner | |
| 5,007,529 A | 4/1991 | Spector | |
| 5,178,839 A | 1/1993 | Spector | |
| 5,313,002 A | 5/1994 | De Heij et al. | |
| 5,432,154 A | 7/1995 | de Heij et al. | |
| D378,126 S | * 2/1997 | Williams | D23/366 |
| 5,908,231 A | 6/1999 | Huff | |
| 5,993,480 A | 11/1999 | Burrows | |
| 6,035,098 A | 3/2000 | Chipalkatti et al. | |
| 6,066,347 A | 5/2000 | Prasad et al. | |

FOREIGN PATENT DOCUMENTS

| | | | | |
|---|---|---|---|---|
| JP | 64-23969 | * | 1/1989 | ................. 219/730 |
| JP | 2-230024 | * | 9/1990 | ................. 219/757 |
| JP | 9-240753 | * | 9/1997 | |
| JP | 2000-85854 | * | 3/2000 | |

OTHER PUBLICATIONS

About—The Human Internet, "How to Clean a Microwave," www.About.com, Jan. 22, 2001, 3 pp.
eGroups, "Creative Home Newsletter," www.egroups.com/message/CreativeHome/50, Jan. 22, 2001, 11 pp.
Google, "How to Remove Smell from Microwave," www.google.com/search, Jan. 22, 2001, 2 pp.
Mrs. Fixit, "Microwave Cleaning," www.nbc33.com/mrs-fixit/microwav.htm, Jan. 22, 2001, 1 p.
"Odors in the Microwave," www.thefrugallife.com/micorwav.htm, Jan. 22, 2001, 2 pp.
The New Homemaker, "Clean and Organized Vinegar: (Almost) The Only Cleaner You'll Ever Need," www.newhomemaker.com/cleanorg/vinegar.html, Jan. 22, 2001, 4 pp.
Tipking, "Fresh Smelling Microwave Oven," www.tipking.com/kitchen/Kit0040.htm, Jan. 22, 2001, 1 p.

* cited by examiner

*Primary Examiner*—Philip H. Leung
(74) *Attorney, Agent, or Firm*—Kenyon & Kenyon

(57) ABSTRACT

A safe and effective microwave deodorizer including a volatile medium, such as a liquid solution of water and citrus oils, contained in an absorbent material such as a non-metallic sponge. When the microwave deodorizer is heated in a microwave oven, the microwave deodorizer releases deodorizing vapors in a manner designed to deposit a deodorizing residue on an inner surface of the microwave oven.

4 Claims, 2 Drawing Sheets

MICROWAVE DEODORIZER

FIELD OF THE INVENTION

The present invention relates to a product and method for deodorizing and freshening a microwave oven.

BACKGROUND INFORMATION

Microwave ovens, as other kitchen appliances such as convection ovens and refrigerators, are subject to becoming odorous from use, and the odors that remain in the microwave oven will affect the flavor and odors of other food that is heated therein. For example, making popcorn in the microwave oven often results in a residual popcorn odor that remains in the microwave oven after the popcorn has been removed. A microwave deodorizer is needed to remove such residual odors from the microwave oven.

Conventional deodorizing methods have been used for kitchen appliances such as microwave ovens, as well as convection ovens and refrigerators. They usually require a user to either manually spread some type of cleaning or deodorizing substance throughout the inner surface of the appliance, with, for example a paper towel. Such methods require substantial manual effort from the user.

Room freshening products and methods have been used which involve heating up the room freshening product in the microwave oven, removing the product from the microwave oven, exposing an inner portion of the product to the ambient air in the room and permitting a vapor generated therefrom to spread throughout the room. However, such products are designed so that the vapors generated therefrom are not released until the product is removed from the microwave oven. The microwave oven remains unaffected.

SUMMARY OF THE INVENTION

The present invention relates to a safe and effective product and method for deodorizing and freshening a microwave oven. The substances used in the product and method will not cling to foods and can be used repeatedly (as often as one needs to deodorize a microwave oven).

In one aspect, the present invention provides a microwave deodorizer including a volatile medium contained in an absorbent material. When the microwave deodorizer is heated within a microwave oven, the microwave deodorizer releases a deodorizing vapor in a manner designed to deposit a deodorizing residue on the inner surface of the microwave oven.

In another aspect, the present invention provides a method for deodorizing a microwave oven including the steps of heating a microwave deodorizer to an elevated temperature within a microwave oven, releasing a deodorizing vapor in the microwave oven and coating an inner surface of the microwave oven with a deodorizing residue formed with the deodorizing vapor contacts the inner surface, where the microwave deodorizer includes an absorbent material and a volatile medium contained therein.

DETAILED DESCRIPTION OF THE INVENTION

The present invention relates to a product and method for deodorizing and freshening a microwave oven, using safe and effective substances which do not cling to foods in the microwave oven and can be used repeatedly (as often as one needs to deodorize a microwave oven).

Figure 1:
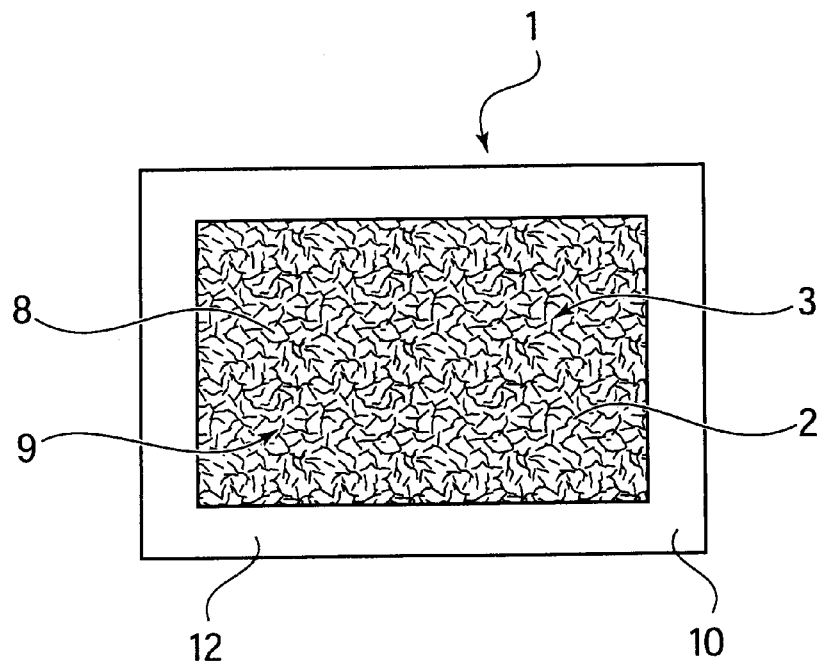
FIG. 1 illustrates a top view of a first embodiment of a microwave deodorizer (without the waterproof cover) according to the present invention.
Figure 2:
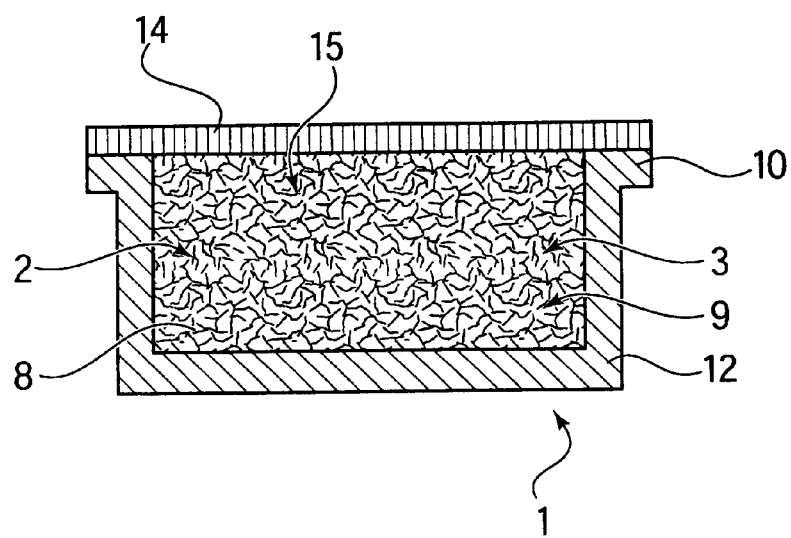
FIG. 2 illustrates a side sectional view of the first embodiment of the microwave deodorizer of FIG. 1.
Figure 3:
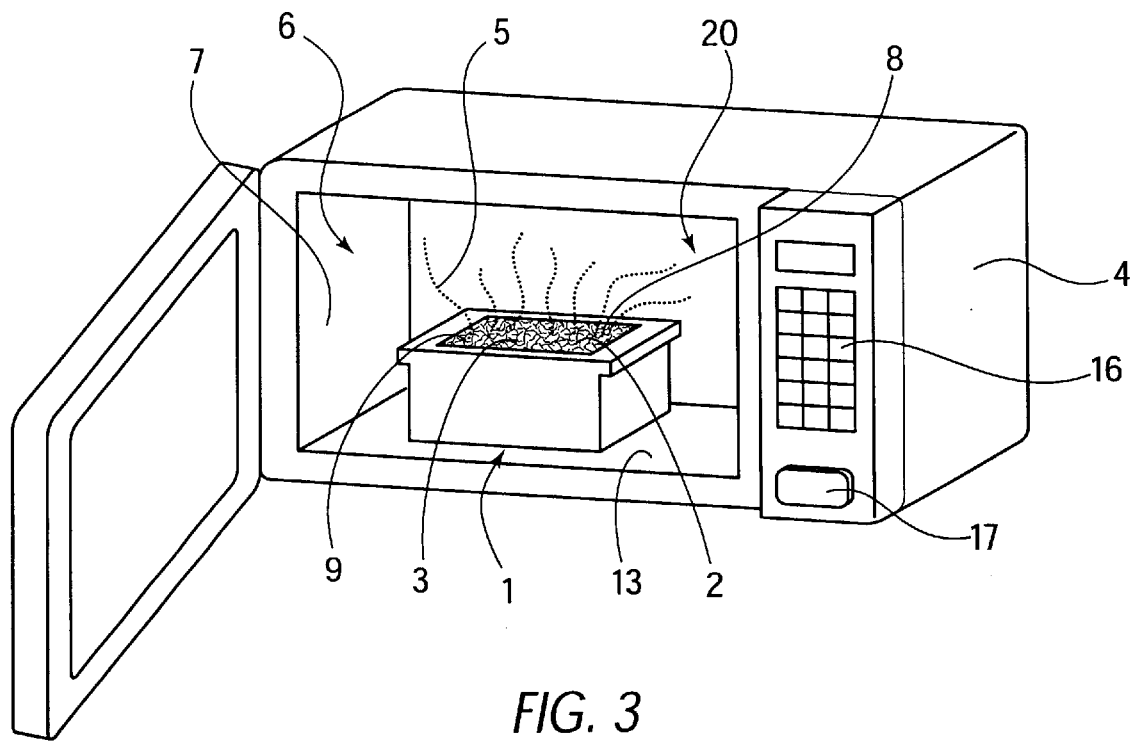
FIG. 3 illustrates a perspective view of the first embodiment of a microwave deodorizer of FIG. 1 in a microwave oven when heated therein.

FIGS. 1–3 show a first embodiment of a microwave deodorizer 1 according to the present invention. As shown in FIGS. 1–3, the microwave deodorizer 1 includes an absorbent material 2, and a volatile medium 3 contained in the absorbent material 2. As shown in FIG. 3, when the microwave deodorizer 1 is heated in a microwave oven 4, the volatile medium 3 is heated to an elevated temperature in a microwave oven 4, and the microwave deodorizer 1 releases a deodorizing vapor 5 in a manner designed to deposit a deodorizing substance or deodorizing residue 6 on an inner surface 7 of the microwave oven 4. In one embodiment, heating the microwave deodorizer 1, heats the volatile medium 3 to an elevated temperature and the deodorizing vapor 5 is released from the volatile medium 3 through the absorbent material 2. The absorbent material 2 provides a more even distribution of the deodorizing vapor 5 and deodorizing residue 6 inside the microwave oven 4. The deodorizing vapor 5 deposits the deodorizing residue 6 on the inner surface 7 upon contact with the inner surface 7.

The absorbent material 2 can be made of a porous, dielectric material, such as a sponge 8 which is non-metallic and may be a natural sponge or a synthetic sponge made of plastic, rubber, cellulose or cotton or a combination thereof. The absorbent material 2 is preferably porous so that it can absorb and sustains the volatile medium 3 contained therein. Dielectric materials are preferable because they are electrically insulating materials, permeable to microwave energy and not heated thereby.

The volatile medium 3 can be a liquid solution 9, made of a mixture of water and citrus oils to give the microwave oven 4 a fresh scent, specifically, for example, a mixture of purified water, lemon oil and orange oil. The sponge 8 may be infused with the liquid solution 9. The volatility of the liquid solution 9 enables it to be readily vaporizable when elevated to a temperature slightly above ambient. The citrus oils in the liquid solution 9 are selected as lossy substances so that the liquid solution 9 has the capability to absorb and/or scatter microwave energy passing therethrough, and thus be heated thereby.

The microwave deodorizer 1 may include a member 10 to hold the sponge 8 (infused with liquid solution 9). The sponge 8 may either rest upon and/or inside the member 10 as shown in FIGS. 1–4. In a first embodiment shown in FIGS. 1–3, the member 10 can an open-ended container 12. The container 12 is designed to rest on a bottom surface 13 of the microwave oven 4 when the microwave deodorizer 1 is placed inside the microwave oven 4, as opposed to having the sponge 8 directly contacting the bottom surface 13 of the microwave oven 4. As with the sponge 8, the container 12 may be made of a dielectric material so that it too is permeable to microwave energy and not heated thereby.

Figure 4:
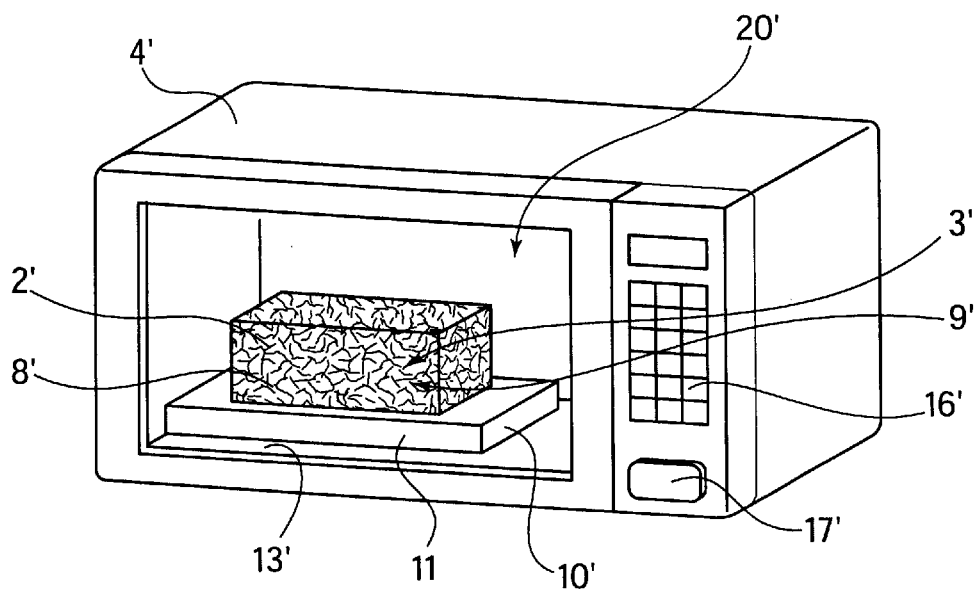
FIG. 4 illustrates a side view of a second embodiment of a microwave deodorizer according to the present invention.

In an alternative embodiment, as shown in FIG. 4, the member 10 can be a flat tray 11. The tray 11 is designed such that sponge 8' rests on tray 11, and tray 11 rests on the bottom surface 13' of the microwave oven 4' when the microwave deodorizer 1' is placed inside the microwave oven 4'. Tray 11 may be made of dielectric material so that it too is permeable to microwave energy and not heated thereby.

In the first embodiment in which the member 10 is a container 12, as shown in FIGS. 1–3, the container 12 can have a waterproof cover 14 covering the open area 15 of the container 12 removably mounted onto the container 12 to prevent any evaporation of the liquid solution 9 before being removed or peeled away from the container 12. The microwave deodorizer 1 can be sold as a completely assembled, ready to use unit made up of the container 12, sponge 8 infused with liquid solution 9, and the waterproof cover 14 covering the open area 15 of the container 12.

A user can optimize the deodorizing properties of the liquid solution 9 before inserting the microwave deodorizer 1 into microwave oven 4 by shaking the container 12 and the sponge 8 infused with liquid solution 9 to emulsify the citrus oils in the liquid solution 9 before removing the waterproof cover 14 from the container 12. Emulsifying the citrus oils in the liquid solution 9 activates the liquid solution 9 by suspending the citrus oils throughout the water, and spreads the liquid solution 9 throughout the sponge 8 so that the heated liquid solution 9 will more evenly coat the inner surface 7 of the microwave oven 4 with the deodorizing substance 6. The user can shake the microwave deodorizer 1 for a short time, e.g., ten (10) seconds, or longer to achieve a more even emulsion of the liquid solution 9.

Once the liquid solution 9 is emulsified, the user could then peel off the waterproof cover 14 from the container 12, and place the container with the sponge 8 and liquid solution 9 in the microwave oven 4. The user may then set the timer 16 on a high setting for a set time period, e.g., four (4) minutes, press the "start" button 17 and let the microwave deodorizer 1 "cook." As described above, the microwave energy absorbed by the liquid solution 9 will raise the temperature of the liquid solution 9 and cause it to release the deodorizing vapor 5, by for example, boiling and emitting the deodorizing vapor 5. The deodorizing vapor 5 may coat the inner surface 7 of the microwave oven 4 with a deodorizing substance 6 when the deodorizing vapor 5 comes into contact with the inner surface 7.

The microwave deodorizer 1 may be designed to be disposable, such that the user may remove it and discard it after use. The user could further optimize the deodorizing properties of the microwave deodorizer 1 by not wiping down the inner surface 7 of the microwave oven 4 after use, but by permitting the deodorizing substance 6 coating the inner surface 7 set overnight.

In practicing a method of the present invention, a method for deodorizing a microwave oven 4 includes the steps of heating a microwave deodorizer 1 to an elevated temperature within the microwave oven 4, releasing a deodorizing vapor 5 in the microwave oven 4 and coating an inner surface 7 of the microwave oven 4 with a deodorizing residue 6 formed with the deodorizing vapor 5 contacts the inner surface 7, where the microwave deodorizer 1 includes an absorbent material 2 and a volatile medium 3 contained therein. The method may also include one or more of the following steps: infusing the absorbent material 2 with the volatile medium 3; placing the absorbent material 2 and volatile medium 3 in a container 12 with a removable waterproof cover 14 covering an open area 15 of the container 12; shaking the container 12 to emulsify a liquid solution of deodorizing oils in the volatile medium 3; removing the waterproof cover 14; and placing the container 12 with the absorbent material 2 and volatile medium 3 in the microwave oven 4 in order to heat the volatile medium 3 in the microwave oven 4.

In the preceding specification, the present invention has been described with reference to specific exemplary embodiments thereof It will, however, be evident that various modifications and changes may be made thereunto without departing from the broader spirit and scope of the present invention as set forth in the claims that follow. The specification and drawings are accordingly to be regarded in an illustrative rather than restrictive sense.

What is claimed is:

1. A microwave deodorizer comprising:

a volatile liquid solution including deodorizing oils therein;

a sponge-like material infused with the volatile liquid solution; and an open-ended container holding the sponge-like material and volatile medium, the open-ended container having a waterproof cover removably mounted thereon, the waterproof cover covering an open area of the open-ended container;

wherein, an emulsion of the deodorizing oils in the volatile liquid solution is created by shaking the microwave deodorizer before removing the waterproof cover, and wherein, when the microwave deodorizer is placed within a microwave oven without the waterproof cover and heated therein, a temperature of the volatile liquid solution is elevated and a deodorizing vapor is released from the volatile liquid solution inside the microwave oven through the sponge-like material in a manner designed to coat an inner surface of the microwave oven with a deodorizing substance when the deodorizing vapor contacts the inner surface of the microwave oven.

2. A method of freshening a microwave oven comprising the steps of:

shaking a microwave deodorizer to emulsify a liquid solution of deodorizing oils contained in an absorbent material therein;

heating the microwave deodorizer to an elevated temperature within a microwave oven;

releasing a deodorizing vapor in the microwave oven; and coating an inner surface of the microwave oven with a deodorizing residue formed when the deodorizing vapor contacts the inner surface.

3. A method of deodorizing a microwave oven comprising the steps of:

placing an absorbent material in a container, the container having an open area exposing an upper surface of the absorbent material to an exterior of the container;

infusing the absorbent material with a volatile medium;

covering the open area with a waterproof cover;

removing the waterproof cover;

placing the container, the absorbent material and volatile medium in the microwave oven;

heating the container, the absorbent material and the volatile medium to an elevated temperature within the microwave oven;

releasing a deodorizing vapor in the microwave oven;

coating an inner surface of the microwave oven with a deodorizing residue formed when the deodorizing vapor contacts the inner surface.

4. A method of deodorizing a microwave oven comprising the steps of:

placing absorbent material in a container, the container having an open area exposing an upper surface of the absorbent material to an exterior of the container;

infusing the absorbent material with a volatile medium;

shaking the container, absorbent material and volatile medium infused therein to emulsify a liquid solution of deodorizing oils in the volatile medium;

heating the container, the absorbent material and the volatile medium to an elevated temperature within the microwave oven;

releasing a deodorizing vapor in the microwave oven; and coating an inner surface of the microwave oven with a deodorizing residue formed when the deodorizing vapor contacts the inner surface.

* * * * *

UNITED STATES PATENT AND TRADEMARK OFFICE
CERTIFICATE OF CORRECTION

PATENT NO.   : 6,444,963 B1
DATED        : September 3, 2002
INVENTOR(S)  : Raymond G. Donahue It is certified that error appears in the above-identified patent and that said Letters Patent is hereby corrected as shown below:

Column 1,
Line 53, change "with" to -- when --;

Column 2,
Line 55, change "can" to -- can be --;

Column 3,
Line 48, change "coating" to -- to coat --;
Line 56, change "with" to -- when --;

Column 4,
Line 5, change "thereof" to -- thereof. --.

Signed and Sealed this

Seventeenth Day of June, 2003

JAMES E. ROGAN
*Director of the United States Patent and Trademark Office*